US006294378B1

(12) United States Patent
Houghton et al.

(10) Patent No.: US 6,294,378 B1
(45) Date of Patent: Sep. 25, 2001

(54) METHOD AND REAGENTS FOR GENETIC IMMUNIZATION

(75) Inventors: Alan Houghton, New York, NY (US); Shirley M. Bartido, Jersey City, NJ (US); Yiquing Xu, New Rochelle, NY (US); Siqun Wang, Wilmington, DE (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/230,199

(22) PCT Filed: Jul. 18, 1997

(86) PCT No.: PCT/US97/12675

§ 371 Date: Jun. 9, 1999

§ 102(e) Date: Jun. 9, 1999

(87) PCT Pub. No.: WO98/04720

PCT Pub. Date: Feb. 5, 1998

Related U.S. Application Data

(60) Provisional application No. 60/022,710, filed on Jul. 26, 1996.

(51) Int. Cl.[7] .......................... C12N 15/63; A61K 31/713
(52) U.S. Cl. .................... 435/320.1; 530/23.4; 514/44
(58) Field of Search .......................... 514/44; 435/320.1; 536/23.4

(56) References Cited

PUBLICATIONS

Struck Vaccine R&D success rates and development times. Nature Biotechnology vol. 14 pp. 591–593, 1996.*

Ulmer et al. Heterologous Protection Against Influenza by Injection of DNA Encoding a Viral Protein. Science. 1993, pp. 1745–1749, vol. 259.

Vijayasaradhi et al. Intracellular Sorting and Targeting of Melanosomal Membrane Proteins: Identification of Signals for Sorting of the Human Brown Locus Protein, GP75. J. Cell Biology. 1995, pp. 807–820, vol. 130.

Tiff et al. The Folding and Cell Surface Expression of CD4 Requires Glycosylation. J. Biological Chemistry. 1992, pp. 3268–3273, vol. 267.

Krishnan et al. Paving the Way Towards DNA Vaccines. Nature Medicine. 1995, pp. 521–522, vol. 1, No. 6.

Nanda et al. Induction of Anti–Self–Immunity to Cure Cancer. Cell, 1995, 13–17, vol. 82.

Rowell et al. Lysosome–Associated Membrane Protein–1–Mediated Targeting of the HIV–1 Envelope Protein to an Endosomal/Lysosomal Compartment Enhances Its Presentation to MHC Class II–Restricted T Cells. J. of Immunology, 1995, 155:1818–1828.

Pardoll et al. Exposing the Immunology of Naked DNA Vaccines. Immunity. 1995, 165–169, vol. 3.

* cited by examiner

*Primary Examiner*—John S. Brusca
(74) *Attorney, Agent, or Firm*—Oppedahl & Larson LLP

(57) ABSTRACT

DNA vaccines which incorporate genetic sequences encoding sorting signals which direct an expressed antigen to a specific cellular organelle facilitate loading of the antigen onto a Class I or Class II MHC molecule for immune presentation. These vaccines are a nucleic acid construct of a genetic sequence encoding a protein or peptide antigen and a sorting signal which will direct expressed antigen to the ER or endosomal-lysosomal compartments within the cell. The resulting constructs can be used as naked DNA vaccines, packaged in liposomes, or coated onto colloidal gold particles. The construct might also be delivered in an expression vector which is expressed in cells of the organism being immunized.

29 Claims, 5 Drawing Sheets

METHOD AND REAGENTS FOR GENETIC IMMUNIZATION

This application is a national phase of International Patent Application No. PCT/US97/12675, filed Jul. 18, 1997, which claims priority from U.S. Provisional Application No. 60/022,710, filed Jul. 26, 1996.

This application relates to improved reagents for use in "genetic immunization," and to a method for genetic immunization which makes use of these reagents to elicit a more potent immune response.

The generation and regulation of immune response is a result of a complex system of interactions between B- and T-lymphocytes, circulating antibodies, and antigen presenting cells (APC). The induction of humoral and cell-mediated immune responses to protein antigens requires the recognition of the antigens by helper T (TH) cells. The reasons for this is that helper T cell are necessary for stimulating B-lymphocyte growth and differentiation, and for activating the effector cells of cell-mediated immunity, including macrophages and cytolytic T lymphocytes (CTLs). Briefly, foreign antigen is processed by APCs which result in the generation of antigen-derived peptide fragments bound to the major histocompatability complex (MHC) Class I and Class II molecules (referred to as human leukocyte antigens or HLA Class I and Class II proteins in humans). These complexes which are found on the cell surface of the APC are then presented to TH cells. Recognition of the peptide-MHC complex by T cells is the initiating stimulus for T cell activation. Thus, more efficient presentation of peptide-MHC complex can lead to more efficient T cell activation. Activation leads to the secretion of cytokines, proliferation, and regulatory or cytolytic effector functions which all lead to immunity, in part through the eradication of cells presenting antigen.

T cell-mediated eradication of cells expressing antigen can be accomplished in three ways. First, humoral responses occur when activated TH cells stimulate the proliferation and differentiation of specific B cell clones to produce antibodies which eventually eliminate cells expressing the antigen as well as extracellular antigen. Second, cell-mediated responses occur when cytokines activate T cells to differentiate into CTLs. The infected target cell is then lysed by the CTL. Endogenous antigens, such as viruses and tumor antigens, activate Class-I restricted CTLs, which lyse cells producing these intracellular antigens. Third, nonspecific responses occur when antigen-activated T cells secrete cytokines that recruit and activate inflammatory cells such as macrophages and natural killer cells that are not specific for the antigen. Overall, therefore, T cells play a central role in recruiting a broad immune response.

As used herein, the term "genetic immunization" refers to the use of DNA as a vaccine to produce an immune response to the protein or peptide antigen encoded by the DNA. Intramuscular administration of naked DNA has been shown to elicit both humoral and cellular immune response. The precise mechanism by which DNA vaccines elicit an immune response is not known, although several possibilities have been discussed. See Pardoll et al., "Exposing the Immunology of Naked DNA Vaccines", *Immunity* 3: 165–169 (1995). Regardless of the mechanism, however, the effectiveness of DNA vaccines to produce both humoral and cellular immunity indicates that naked DNA is expressed after administration, with the protein or peptide product being presented as an antigen in association with either Class I or Class II proteins.

The processing and presentation of antigens by Class I and Class II molecules occurs in different organelles within the cells. Specifically, the endoplasmic reticulum (ER) has been shown to be the site for loading peptide antigens derived from the cytoplasm onto Class I molecules, while the endosomes/lysosomes have been shown to be the site for loading peptide antigens onto Class II molecules. Thus, the type of immune response and the extent to which an immune response is generated may depend in significant measure on the amount of antigen reaching the ER and endosomal loading sites. It would therefore be highly advantageous to be able to direct and control the accumulation of antigen within a desired location within the cell to provide optimum immune response.

It is an object of the present invention to control the trafficking to and stability of selected antigens within specific cellular organelles, and to use this method to provide for enhanced genetic immunization.

It is a further object of the present invention to provide DNA vaccines which incorporate genetic sequences encoding sorting signals which direct the expressed antigen to a specific cellular organelle and facilitate loading of the antigen onto a Class II or Class II MHC molecule for immune presentation.

It is still a further object of the invention to provide a method for genetic immunization utilizing DNA vaccines which incorporate genetic sequences encoding sorting signals which direct the expressed antigen to a specific cellular organelle and facilitate loading of the antigen onto a Class I or Class II MHC molecule for immune presentation.

SUMMARY OF THE INVENTION

These and other objects of the invention are achieved through the construction of a genetic sequence encoding a protein or peptide antigen and a sorting signal which will direct expressed antigen to the ER or endosomal-lysosomal compartments within the cell. The resulting constructs are useful as DNA vaccines, and can be used as naked DNA, packaged in liposomes, or coated onto colloidal gold particles. The construct might also be delivered in an expression vector, for example a viral vector, which is expressed in cells of the organism being immunized.

DETAILED DESCRIPTION OF THE INVENTION

In accordance with the present invention, nucleic acid constructs for use in genetic immunization procedures are prepared which comprise (a) an antigen-coding region encoding an antigenic protein or peptide; and (b) a sorting region encoding a protein or peptide which acts as a sorting signal to direct intracellular transport of the protein or peptide to the endosomal-lysosomal compartments or their transport to/retention in the endoplasmic reticulum of a cell. As used herein, the term "nucleic acid construct" reflects the fact that the material is produced from component parts that are spliced together from different sources and excludes, for example, a DNA molecule encoding a naturally occurring protein that includes both an antigenic determinant and a sorting signal region.

The antigen-coding region of the nucleic acid polymers of the invention is selected to encode for one or more desired antigenic determinants of a protein or peptide of interest. Thus, the antigen-coding region may encode an entire protein or peptide, or an immunogenic portion thereof associated with a selected epitope of the protein or peptide.

Figure 5:
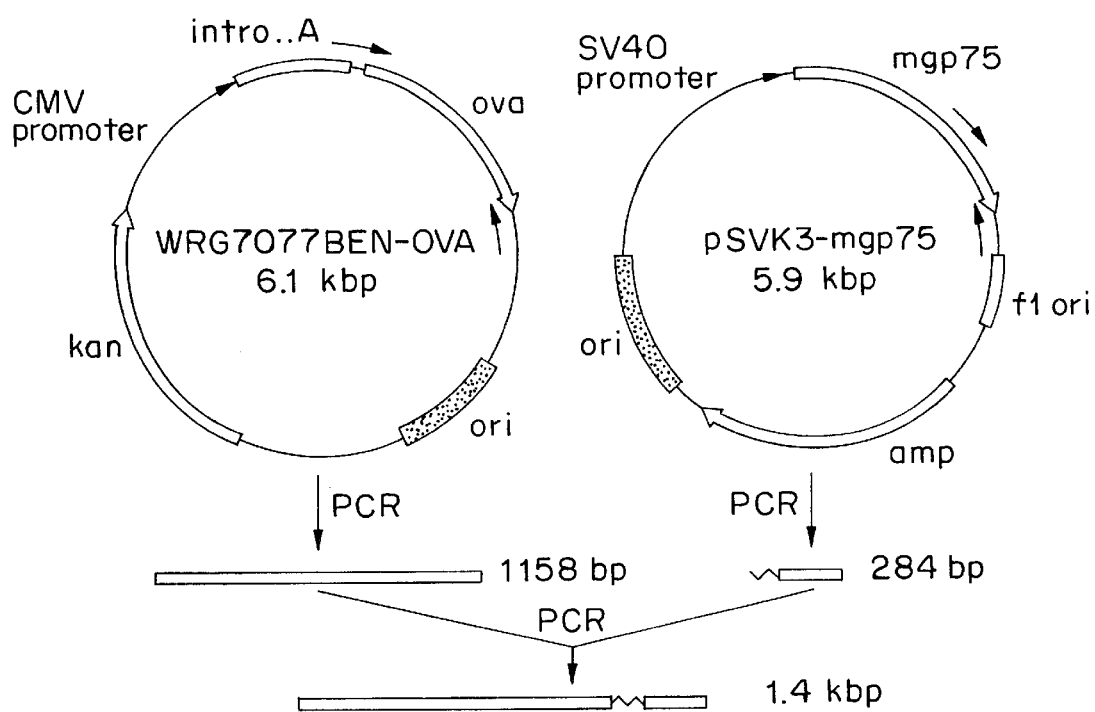
FIG. 5 shows a method for forming a nucleic acid construct in accordance with the invention.

The sorting region employed in the nucleic acids polymers of the invention is selected to provide a peptide region that directs intracellular transport of an expressed protein or peptide to a desired intracellular location. Suitable sorting signals for directing intracellular transport of the expressed antigen to the endosomes include the following molecules: the signal from human gp75 (brown locus protein) which includes the signal region Glu Ala Asn Gln Pro Leu Leu Thr Asp; SEQ ID No. 1 the signal from human tyrosinase (albino locus protein) which includes the signal region Glu Glu Lys Gln Pro Leu Leu Met Asp; SEQ ID No. 2 the signal from human gp100 (silver locus protein, Pmel 17) which includes the signal region Glu Asp Ser Pro Leu Leu; and SEQ ID No. 3 the signal from human P-protein (pink eyed locus) which includes the signal region Glu Asp Thr Pro Leu Leu SEQ ID No. 4 as described in Vijayasaradhi et al., "Intracellular Sorting and Targeting of Melanosomal Membrane Proteins: Identification of Signals for Sorting of the Human Brown Locus Protein, GP75" *J. Cell Biology* 130: 807–820 (1995).

Suitable sorting signals for directing intracellular transport of the expressed antigen to the endoplasmic reticulum (or retention therein) include the signal region Pro Ser Arg Asp Arg Ser Arg His Asp Lys Ile His SEQ ID No. 5 which has been shown to retain a viral glycoprotein in the endoplasmic reticulum. Rose et al. "Altered cytoplasmic domains affect intracellular transport of the vesicular stomatitis virus glycoprotein" *Cell* 34: 513 (1993); Bartido et al. "Processing of a viral glycoprotein in the endoplasmic reticulum for class II presentation" *Euro. J. Immunol.* 25: 22111–2219 (1995).

Mutant forms of naturally-occurring sorting signal-containing proteins and peptides may also be used as the sorting region of the invention. Such mutants can alter protein or peptide trafficking by making the protein or peptide more unstable in a particular compartment in the cell, including the ER and endosome/lysosome. For example, because glycosylation plays an important role in stabilizing endocytic membrane proteins within different cellular compartments, glycosylation mutants can be used to more closely control the intracellular transport of the expressed antigen/sorting signal product to induce the desired form of immune response. On any given protein, there will generally be multiple glycosylation sites, with each site being of different importance in its effect on the transport and degradation of the protein. For example, in the case of mouse gp75, there are five N-glycosylation sites, one of which strongly effects the resistance to protease digestion and two others of which are important for permitting export of the protein from the endoplasmic reticulum. Other mutants forms, for example mutants forms which disrupt the sorting signal regions described above, particularly the Pro Leu Leu motif, can also be used in the method of the invention. Constructs which have a sequence which is the same as the wild-type sequence for a sorting signal, or which are a mutant variant of such a wild-type, or which are synthetically generated to encode the same protein/peptide sequence as the wild-type or mutant variants based upon degeneracy of the nucleic acid code are referred to in the specification and claims hereof as being "derived from" the wild type protein or peptide.

Identification of suitable mutants can be identified by creation of the desired mutant, for example by site-directed mutagenesis, followed by testing of each mutant in a model system. For example, in the case of gp75, the two mutant forms shown in FIG. 1 were compared to the wild-type mutant. The sorting signal peptide labeled as "Deletion" has a deletion mutation introduced in the region spanning Asn 511 to Asp 517, which results in the deletion of the sorting signal region. The sorting signal peptide labeled L2A differs from the wild-type by a single base substitution, Leu514 to Ala514 which disrupts the Pro Leu Leu motif of the sorting signal.

Testing of the ova/gp75 constructs shown in FIG. 1 for their ability to induce an immune response to ova in mice showed differential results depending on the sorting signal employed. As shown in FIGS. 2 and 3, the construct containing the wild-type sequence produced a MUCH greater $CD4^+$ T Cell response, while the constructs containing the mutant sequence produced higher levels of IgG response. Both the fusion protein containing the wild-type sequence and the fusion protein containing the L2A mutation were effective to provide protection against tumor cells expressing ovalbumin. (FIG. 4).

Glycosylation-mutants of sorting signals can be similarly prepared and tested for their ability to direct the trafficking of the expressed fusion proteins to desired regions within the cell. Mutations at two of the five identified glycosylation sites on mouse gp75 (Asn304 and Asn385) produced proteins which are apparently retained and degraded in the endoplasmic reticulum. Such mutant sorting signals can be used in fusion proteins in accordance with the invention to selectively generate peptides for the MHC Class I pathway. A third mutant form (Asn350) was transported from the ER to the Golgi apparatus at a similar rate to the wild-type but exhibited a markedly decreased half-life, being very unstable in endosomes. Such mutants can be used in fusion proteins to direct an MHC Class II response, and the enhanced degradation of the sorting signal may generate more peptides for presentation through this pathway. Mutation at Asn181 of mouse gp75 impacted the rate of transport with the result that the mutant protein tended to localize in the endosomal/lysosomal structures of the transfectants and not in the Golgi apparatus. Fusion proteins with sorting signals of this type can also be used to direct an MHC Class II response to the antigen.

The antigen-coding region and the sorting region are combined into a single nucleic acid polymer which may optionally contain a linker region to ensure proper folding of the encoded fusion protein. One suitable technique for this process utilizes initial separate PCR amplification reactions to produce the two regions, each with a linker segment attached to one end, followed by fusion of the two amplified products in a further PCR step using the general scheme shown in FIG. 5. This technique is referred to as linker tailing. Of course, it will be appreciated that other techniques and variations on this technique can be used. For example, when either the antigen-coding region or the sorting region is fairly short, the region may be chemically synthesized and coupled to the other region by ligation. Suitable restriction sites may also be engineered into regions of interest, after which restriction digestion and ligation is used to produce the desired fusion-protein encoding sequence.

After synthesis, the nucleic acid polymer containing both the antigen-coding region and the sorting region is combined with a promoter which is effective for expression of the nucleic acid polymer in mammalian cells. This can be accomplished by digesting the nucleic acid polymer with a restriction endonuclease and cloning into a plasmid containing a promoter such as the SV40 promoter, the cytomegalovirus (CMV) promoter or the Rous sarcoma virus (RSV) promoter. The resulting construct is then used as a vaccine for genetic immunization. The nucleic acid polymer could also be cloned into plasmid and viral vectors that are known to transduce mammalian cells. These vectors include retroviral vectors, adenovirus vectors, vaccinia virus vectors, pox virus vectors and adenovirus-associated vectors.

The nucleic acid constructs containing the promoter, antigen-coding region and sorting region can be administered directly or they can be packaged in liposomes or coated onto colloidal gold particles prior to administration. Techniques for packaging DNA vaccines into liposomes are known in the art, for example from Murray, ed. "Gene Transfer and Expression Protocols" Humana Pres, Clifton, N.J. (1991). Similarly, techniques for coating naked DNA onto gold particles are taught in Yang, "Gene transfer into mammalian somatic cells in vivo", Crit. Rev. Biotech. 12: 335–356 (1992), and techniques for expression of proteins using viral vectors are found in Adolph, K. ed. "Viral Genome Methods" CRC Press, Florida (1996).

The compositions of the invention are preferably administered intradermally, subcutaneously or intramuscularly by injection or by gas driven particle bombardment, and are delivered in an amount effective to produce an immune response in the host organism. The compositions may also be administered ex vivo to blood or bone marrow-derived cells (which include APCs) using liposomal transfection, particle bombardment or viral infection (including co-cultivation techniques). The treated cells are then reintroduced back into the mammal to be immunized. While it will be understood that the amount of material needed will depend on the immunogenicity of each individual construct and cannot be predicted a priori, the process of determining the appropriate dosage for any given construct is straightforward. Specifically, a series of dosages of increasing size, starting at about 0.1 ug is administered and the resulting immune response is observed, for example by measuring antibody titer using an ELISA assay, detecting CTL response using a chromium release assay or detecting TH response using a cytokine release assay.

The invention will now be further described and illustrated by was of the following, non-limiting examples.

EXAMPLE 1

To demonstrate the creation of a nucleic acid construct in accordance with the invention, a construct having an antigen-coding region encoding chicken ovalbumin and a sorting region derived from murine gp75 was produced. In the construct, the chimeric protein of full length ovalbumin and the C-terminal region of gp75 containing the sorting sequence Glu Ala Asn Pro Leu Leu Thr Asp SEQ ID No. 1 are connected with a nine amino acid linker, Ser Gly Gly Ser Gly Gly Ser Gly Gly. SEQ ID No. 6

The construct was prepared using a series of PCR reactions. First, the ovalbumin gene coding amino acids 1–386 was amplified from pAc-neo-OVA (Moore et al., "Introduction of Soluble Protein into the Class I Pathway of Antigen Processing and Presentation" Cell 54: 777–785 (1988)) with the primer pair 5'-CGCCACCAGACATAATAGC-3' and SEQ ID No. 7

5'-GCCTCCTGAACCTCCGGAACCACCAGAAG \GGGAAACACATCTGCC-3'. SEQ ID NO. 8

The transmembrane and cytoplasmic domains of gp75, amino acid 488–539, were then amplified out from pSVK3-mpg75 (Vijayasaradhi et al., J. Cell Biol. 130: 807–820 (1995) using primers 5'-TCTGGTGGTTCCGGAGGTTCAGGAGGCAT CATTACCATTGCTGTAGTG-3' SEQ ID No. 9 and 5'-GGTTGCTTCGGTACCTGCTGCG-3'. SEQ ID No.10

The PCR products from these two amplification were purified and subjected to a second round of PCR using primers 5'-CGCCACCAGACATAATAGC-3' (SEQ ID NO. 11) and 5'-GGTTGCTTCGGTACCTGCTGCG-3' (SEQ ID No.12). (See FIG. 5) The second phase of the PCR fused the ova and gp75 sorting region with the designed linker in between. Thus, the construct has a combined open reading frame of 1365 base pairs capable of coding a protein a protein of 455 amino acids which includes 386 amino acids from ovalbumin, 9 amino acids from the linker and 60 amino acids from gp75.

Figure 6:
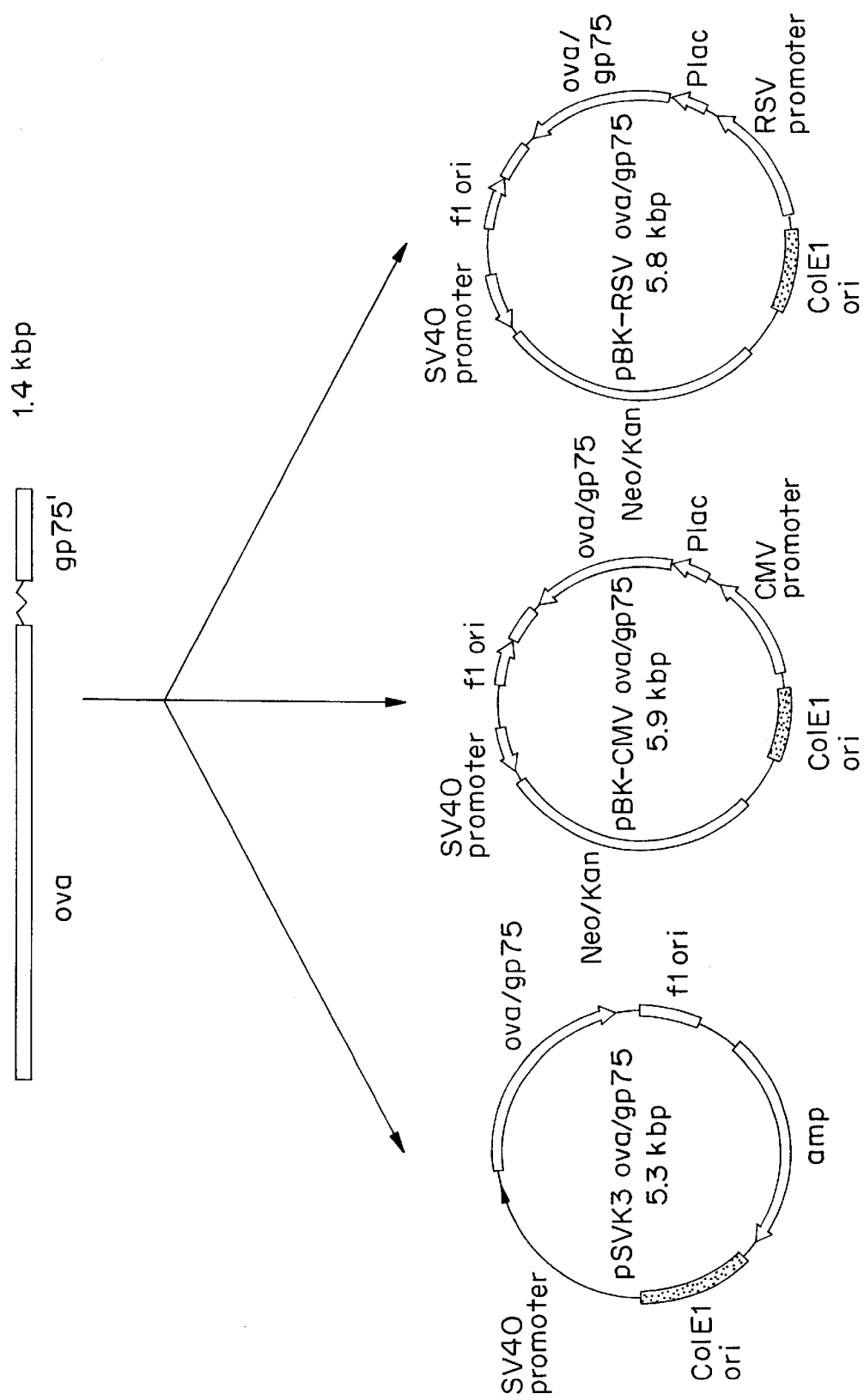
FIG. 6 shows the construction of three different plasmids containing a construct in accordance with the invention.

The construct was digested with EcoR1 and Kpn1 and cloned into pSVK3 (Pharmacia/LKB Ltd.), pBK-CMV and pBK-RSV (Stratagene Inc.) separately as shown in FIG. 6. These constructs have been sequenced and their structures have been confirmed.

Figure 1:
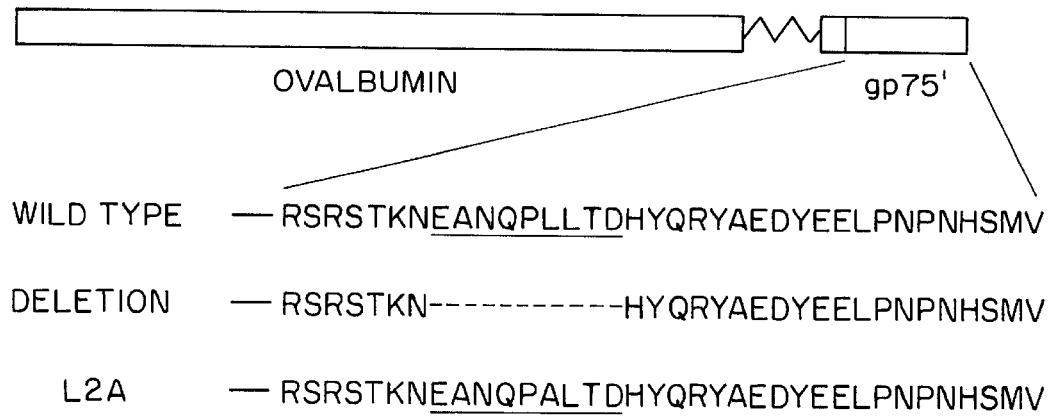
FIG. 1 shows three forms of an ovalbumin/gp75 fusion protein.

To construct targeting derivative mutants, PCR primers containing mutations were synthesized. They are 5'-CTCAGCATAGCGTTGATAGTGATTCTTGG TGCTTCTAGAACG-3' SEQ ID No 13 and 5'-CGTTCTAGAAGCACCAAGAATCACTATC AACGCTATGCTGAG-3' (SEQ ID No. 14) for the deletion of Asn511 to Asp517 mutant. The primer pair 5'-GAGTGCAGGCTGGTTGGCTTC-3' (SEQ ID No. 15) and 5'-CCTGCACTCACTGATCACTAT3' (SEQ ID NO.16) are used to construct the Leu514 to Ala514 mutant (FIG. 1). These constructs have been sequenced and their structures have been confirmed.

EXAMPLE 2

Expression of the fusion protein as well as that of ovalbumin alone was examined by utilizing plasmids that contained the encoding DNA under different promoters. The DNA was transiently transfected into mouse L cells or monkey COS cells by calcium phosphate precipitation or DEAE-chloroquine methods. The cells ($1 \times 10^5$) were plated on a 8-well chamber slide (Nunc, Inc.) and incubated for 24 hours. Cells were then transfected with 0.5–1.0 µg DNA by known standard calcium phosphate or DEAE methods. After transfection, cells were allowed to grow for 24–48 hours prior to determining the intracellular localization of ovalbumin in the transfected cell.

Detection of the protein was carried out by immunofluorescent staining of the antigen. Cells were washed with cold phosphate buffered saline (PBS), fixed with 2% formaldehyde, permeabilized with methanol at −20° C. and then incubated with the monoclonal antibody (mAb) OVA-14 (BioMaker Inc.). The cellular localization of the antigen was then visualized by staining with a secondary antibody, FITC-conjugated goat anti-mouse antibody (Dako, Inc.). The cells were observed using a Nikon microscope and photographed using back and white film, ISO100.

Expression of the protein ovalbumin or of the fusion protein gp75-ova was observed upon transfection of the DNA constructs into cells using all three promoters (SV40, CMV and RSV). Furthermore, when plasmids which included gp75 sorting region were introduced into the cells, localized vesicular immunofluorescent staining was observed consistent with endosome-lysosome localization. In contrast, when the control plasmids without the gp75 sorting region were introduced, a more diffuse cytoplasmic staining pattern typical of staining of Golgi/ER localization was observed. Thus, incorporation of the gp75 sorting region dramatically changed the intracellular trafficking of a protein, ovalbumin, destined for the secretory pathway to a protein contained in a vesicular compartment in the endocytic pathway.

EXAMPLE 3

To test the ability of the constructs encoding the OVA/gp75 fusion protein to act as a vaccine for genetic immunization, (C57BL/6×Balb/c) F1 mice were immunized with respective DNA plasmids purified by using QIAGEN ion-exchange columns (Qiagen, Inc.). DNA (100 µg in 100 µl of a 25% sucrose solution in PBS) was injected subcutaneously at day 0 and day 14. Blood samples were collected at day 14 and day 28.

Figure 7:
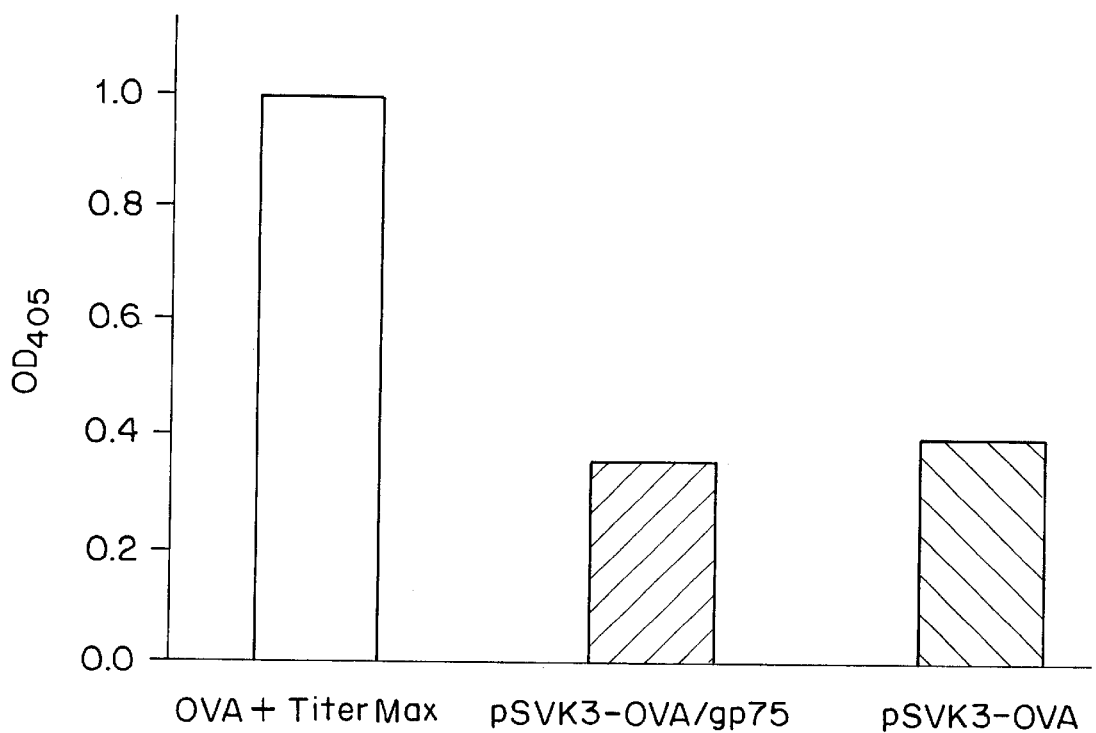
FIG. 7 shows a graphical representation of the immune response generated upon immunization with a construct in accordance with the invention.

Antibody response was monitored using an ELISA assay. Chicken ovalbumin (Sigma, Inc.) was used as the antigen and plated in a 96-well plate overnight at 4° C. The diluted serum samples were then added to the plate and incubated for 1 hour at room temperature. After washing, the secondary antibody, alkaline phosphatase-conjugated goat anti-mouse IgG, was added and plate was incubated for 1 hour. Color development was achieved upon addition of the Sigma Fast p-nitrophenyl substrate. Reaction was terminated with the addition of 3N NaOH. Absorbance in the different wells was obtained using the BioRad EIA Reader 2550. Results are shown in FIG. 7. As can be seen, the genetic immunization technique using the constructs of the invention was effective to produce antibodies to ovalbumin. Corresponding plasmid constructs with different promoters also elicited an immune response, although not as strongly as that seen when using the SV40 promoter.

EXAMPLE 4

CBF1 mice were immunized with DNA plasmids purified by the QIAGEN ion-exchange columns (Qiagen, Inc.). To prepare bullets for immunization, 50 mg of 0.95–2.6 µm gold particles (Auragen, Inc.) were mixed with 0.05–0.1 M spermidine, 100 µg of plasmid DNA was added to the mixture, and 1.0–2.5 M $CaCl_2$ was added dropwise while vortexing. After precipitation, the gold/plasmid DNA complex was washed three times with cold 100% ethanol. Seven ml of ethanol was added to the pellet to achieve a bead loading rate of 0.5 mg gold and 1.0 µg plasmid DNA per injection. The gold/plasmid DNA solution was then instilled into plastic Tefzel® tubing, the ethanol gently drawn off, and the tube purged with nitrogen gas at 400 ml/min for drying. The tube was cut into 0.5 inch bullets and these were used for immunization. For cutaneous immunizations, all mice were anesthetized with Metofane inhalation (Pitman-Moore, Mundelein, Ill.). Abdominal hair was removed with Nair® depilatory cream (Carter-Wallace, New York, N.Y.), so that depilated abdominal skin was exposed for immunization. The bullets were placed into a hand-held helium-driven gene gun (Auragen, Inc.). Animals were immunized by delivering the gold beads in one bullet into each abdominal quadrant, for a total of four injections per immunization. Each injection delivered 1 µg DNA and therefore a total of 4 µg DNA per mouse each immunization. Each bullet was delivered to the abdominal skin at a helium pressure of 400 pounds per square inch.

Figure 3:
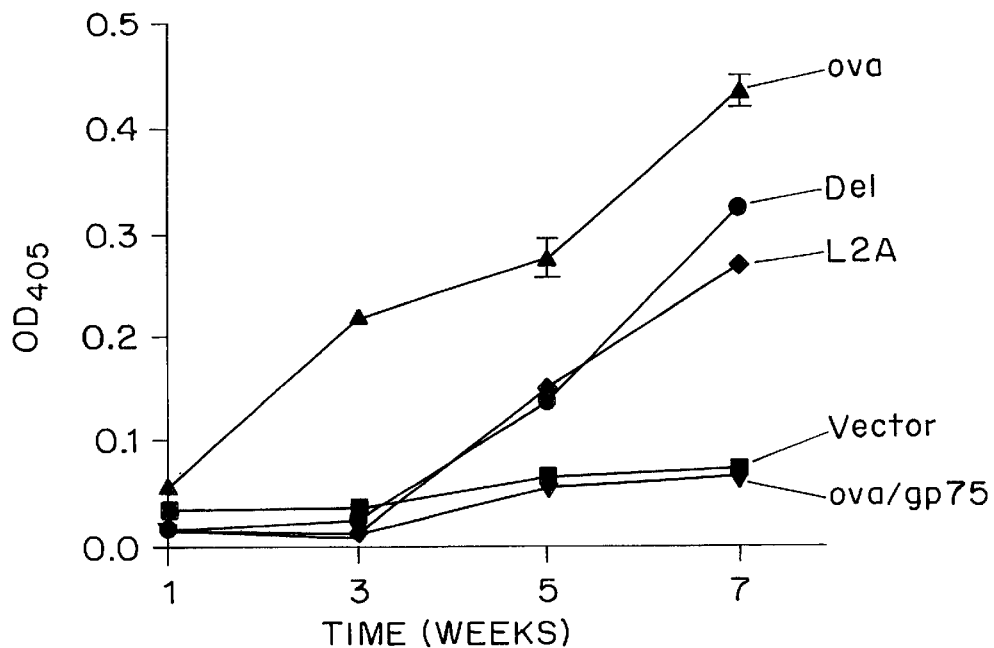
FIG. 3 shows the induction of an IgG response using the invention.

In vivo antibody response. Indirect ELISA assays were performed to monitor the antibody response. CB6F1 mice were immunized with different plasmid constructs by gene gun once a week for four weeks and a boost at week 6. Serum samples were collected at weekly intervals. Purified chicken ovalbumin (Sigma, Inc.) was used as the antigen and plated 50 µg each well in a 96-well plate overnight at 4° C. The diluted serum samples were then added to the plate and incubated for 1 hour at room temperature. After washing, the second antibody goat anti-mouse IgG conjugated with alkaline phosphatase (Sigma, Inc.) was added and incubated for 1 hour at 37° C. The plates were developed using the Fast p-Nitrophenyl phosphate substrate (Sigma, Inc.) and the reactions were terminated with the addition of 3N NaOH. The absorbance at 605 nm were obtained by the BioRad EIA Reader 2550 (BioRad Inc.). The positive control group immunized with naked DNA containing the full length ovalbumin generated strong response within 2 weeks (FIG. 3). Mutants with a disrupted (L2A) or deleted (del) sorting signal also generated antibody response although the response appeared to be delayed comparing to the wild type ovalbumin. Interestingly, the ova/gp75 fusion protein failed to generate an antibody response under the particular immunization protocol. The reason for that is not known. But it is conceivable that most of the fusion protein is sequestered in the cell due to its retention signal at the c-terminus and not efficiently recognized by the B cells.

Figure 2:
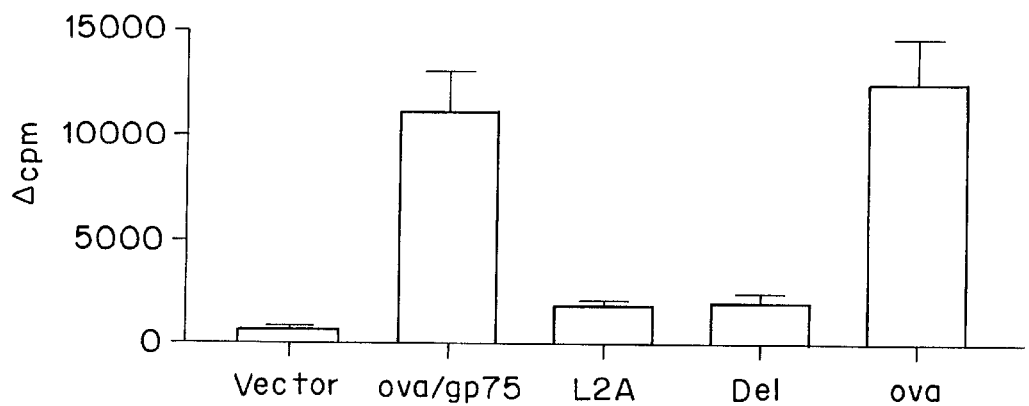
FIG. 2 shows the induction of CD4+ T cell response using the invention.

CD4+ T cell proliferative assay. A proliferation assay was carried out to monitor the efficiency of in vivo priming of CD4+ T cells by the different DNA constructs. CB6F1 mice were immunized once a week for two weeks by gene gun and at day 14 the mice were sacrificed. CD4+ T cells were purified from pooled splenocytes using a CELLECT™•PLUS column (Biotex Laboratories, Inc.). The purified CD4+ T cells ($3 \times 10^5$) were in vitro stimulated by incubation with syngeneic naive splenocytes ($1 \times 10^5$) pulsed with the denatured ovalbumin at different concentrations for 4 days at 37° C. On day 4, 100 µCi of $^3$H-TdR was added to each well and the cpm is counted after 16–18 hours. The proliferation response is expressed as the net cpm subtracting the background (FIG. 2). The ova/gp75 fusion efficiently primed T cells in vivo suggesting the endogenous processing and presentation of the fusion protein. Moreover, melanosomal targeting mutants, L2A and Del, did not prime well demonstrating the requirement of the targeting signal for the function of the fusion protein in stimulating CD4+ T cell prliferation.

Figure 4:
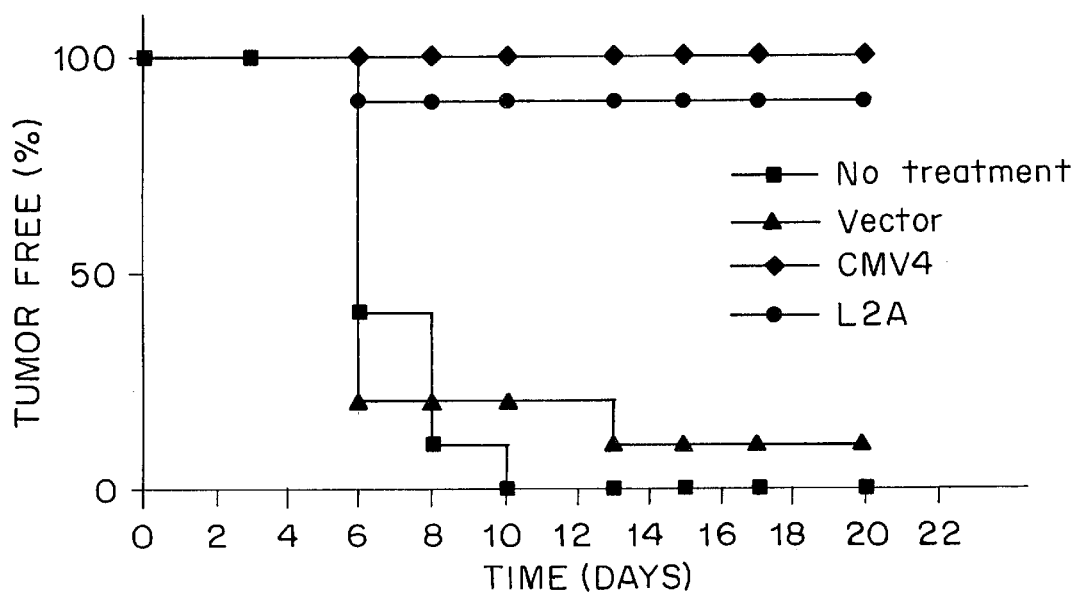
FIG. 4 shows the affect of genetic immunization in accordance with the invention on tumor growth in mice.

Tumor protection. CB6F1 mice were immunized weekly for two weeks with pBK-CMV vector alone, the vector containing the ova-gp75 construct of FIG. 1 or the vector containing the ova/L2A construct. On day 14, the immunized mice were challenged by injecting subcutaneously with 1×10⁶ MO4 melanoma cells, a B16 melanoma cell line transfected with the fill length ovalbumin. Mice were checked for tumor growth every other day over a period of 3 weeks. The "no treatment" group (n=10) all developed palpable tumor within 2 weeks. Similarly, of the mice immunized with the vector alone (n=10), all but one developed tumor. None of the mice immunized with the vector encoding the ova/gp75 fusion protein (n=10) developed tumor and only one out of ten developed tumor in the L2A group (FIG. 4). This result clearly shows that the immune response elicited by immunization with fusion protein construct can lead to protection of tumor challenges in vivo.

To test the whether immunization by this method induced immunologic memory, mice immunized with the fusion DNA were re-challenged with tumor MO4 or B16 melanoma (the parent melanoma cell line of MO4 that does not express the antigen ovalbumin) five weeks after the last immunization. None of the five mice challenged with MO4 developed tumor when observed for at least six weeks, and two of the five mice challenged with B16 parental melanoma did not develop tumor over at least 6 weeks. All five unimmunized mice challenged with B16 developed tumors within 10–14 days. The sorting signal was required for protection against B16 parental tumor. Five mice immunized with the DNA construct containing a mutant sorting signal (L2A) all developed tumor when challenged with B16. The sorting signal was also required for potent immunological memory, because one out of four mice immunized with construct containing mutant sorting signal (L2A) developed tumor with MO4 tumor challenge. This experiment show that immunization with DNA constructs containing the tyrosinase family sorting signal can provide long lasting memory against the antigen and can even provide a broader protection against tumor challenge in tumors that do not express the antigen.

EXAMPLE 5

To identify the sorting signal, constructs were made having an antigen-coding region encoding the extracellular domain of the T lymphocyte surface glycoprotein CD8, and a sorting region containing the cytoplasmic tail of the human gp75 (amino acids 497 to 537) or the cytoplasmic tail and the transmembrane domains (TM) of human gp75 (amino acids 477 to 537). To make these constructs, a full-length 2.8 kb EcoRI fragment was isolated from a human melanoma cDNA library and subcloned into the unique EcoRI site of eukaryotic expression vectors pCEXV3 (Bouchard et al., *J. Exp. Med.* 169: 2029–2042 (1989)) or pSVK3.1 (a derivative of vector pSVK3 obtained by deletion of the Sac I fragment within the multiple cloning site), or SmaI site of pSVK3 (Pharmacia LKB, Piscataway, N.J.) following a fill-in reaction with Kienow fragment of DNA polymerase (New England Biolabs, Beverly, Mass.). The orientation of the cloned insert was determined by restriction analysis and confirmed by dideoxy chain termination sequencing method (Sequenase Kit, US Biochemicals, Cleveland, Ohio) using an oligonucleotide primer complementary to the vector sequences upstream of the cloning site.

Mouse L cell fibroblasts were transfected with plasmid containing gp75 cDNA and pSV2neo. Transfected clones were isolated by selecting for growth in the antibiotic G418 (1 mg/ml; Gibco BRL, Gaithersburg, Md.), and screened for gp75 expression by immuno-fluorescence staining with the mAb TA99 (Vijayasaradhi et al., *Exp. Cell Res.* 171: 1375–1380 (1991)).

The plasmid EBO-pCD-Leu2 containing human CD8α cDNA was obtained from American Type Culture Collection (Margolskee et al., 1988). The 2.3 kb BamHI fragment from this plasmid was isolated, made blunt-ended with Klenow fragment and cloned into the SmaI site of the expression vector pSVK3. The orientation of the cDNA insert in the recombinant plasmids in *E. coli* DH5α was analyzed by appropriate restriction enzyme digestions, and confirmed by DNA sequencing.

Chimeric cDNAs encoding fusion proteins CD8/gp75 (TM+Cyt) and CD8/gp75(Cyt) were constructed by the following methods. First, appropriate restriction sites at or near the TM/Cyt junction of CD8, and lumenal/TM and TM/Cyt junctions of gp75 were generated by site-directed mutagenesis (Kunkel et al., 1987) using Mutagene kit (BioRad Laboratories, Hercules, Calif.). Specifically, a mutant gp75 plasmid pSVgp75RV was generated by introducing an EcoRV restriction site at nucleotide 1560 (lumenal/TM junction) of gp75 cDNA in plasmid pSVK3 using the mutagenic oligonucleotide 5'-TACTGCTATGGCAATGA TATCAGGTACACTA-3
SEQ ID No. 17

(mutations introduced are shown in bold and underlined). This resulted in the conversion of glutamic acid at position 477 (amino acids numbered starting with the methionine coded by the initiation codon) to aspartic acid. Mutant plasmids pSVgp75H and pSVleu2H were generated by introducing a HindIII restriction site in gp75 cDNA at nucleotide 1627, (gp75 TM/Cyt junction) and at nucleotide 706 (CD8 TM/Cyt junction) in CD8 cDNA using the mutagenic oligonucleotides 5'-GCGTCTGGCACGAAGCTTATAAGAAGCAGT-3'
and SEQ ID No. 18

5'-GTCTTCGGTTCCTAAGCTTGCAGTAAAGGGT-3',
SEQ ID No. 19 respectively. This resulted in conversion of leucine at position 500 to lysine and isoleucine at 501 to leucine in gp75; and asparagine at 207 to lysine and histidine at 208 to proline in CD8. Mutants were first identified by appropriate restriction enzyme digestion and confirmed by sequencing the relevant regions of the plasmids using a Sequenase sequencing kit. Transient expression in mouse fibroblasts and immunofluorescence analysis with mAbs TA99 (anti-gp75) and OKT-8 (anti-human CD8) showed that intracellular staining of mutant proteins was identical to the distribution of wild type counterparts, I.e., punctuate cytoplasmic staining of gp75 and cell surface expression of CD8.

Plasmid pSVgp75RV was digested with EcoRV and XbaI to produce a ≈1.2 kb fragment containing the TM+Cyt sequence and 3' untranslated sequence of gp75 cDNA including part of the multiple cloning site sequences of the vector; plasmid pSVleu2H was digested with EcoRV and XbaI and the large ≈4 kb plasmid DNA fragment lacking TM and Cyt sequences of CD8 cDNA was isolated. The 1.2 kb EcoRV-XbaI gp75 fragment was ligated with the large EcoRV-XbaI pSVleu2H fragment to generate a plasmid construct encoding the fusion protein CD8/gp75 (TM+Cyt). Similarly, a ≈1 kb HindIII-XbaI gp75 cDNA fragment (containing gp75 Cyt and 3' untranslated sequences), and a ≈4 kb HindIII-XbaI CD8 cDNA plasmid fragment (lacking the cytoplasmic tail sequences of CD8) were isolated, respectively, from plasmids pSVgp75H and pSVleu2H, and ligated to generate the fusion protein CD8/gp75(Cyt). Regions of the plasmids at the CD8/gp75 junctions were sequenced from at least two independent clones to confirm the restoration of the reading frame. Large scale plasmid preparations (Quiagen, Inc., Chatsworth, Calif.) were further verified by restriction enzyme digestions for the presence of enzyme sites unique to gp75 and CD8 at appropriate regions in the chimeric plasmids.

pSVK3.1gp75, was utilized to generate carboxyl terminal deletion mutants. The restriction enzyme site BglII at nucleotide 2000 of gp75 cDNA is a unique site within the plasmid pSVK3.1. Plasmid pSVK3.1 gp75 (10 μg) was linearized by digestion with 40 units of BglII in a 50 μl reaction for 3 h at 37° C. Linearized ≈6.7 kb DNA was then digested for 3–4 min with Bal 31 nuclease (1 unit enzyme/μg DNA) in 50 μl reaction. Digested DNA was immediately extracted with phenol:chloroform to inactivate and remove the nuclease, and the ends were filled in by Kienow fragment of DNA polymerase I to increase the population of blunt-ended molecules (Sambrook et al., 1989). Klenow fragment was inactivated by heating at 75° C. for 10 min, and a suppressible reading frame termination linker containing restriction site NheI, 5'-CTAGCTAGCTAG-3' (Pharmacia), was ligated to the blunt-ended, truncated pSVK3.1 gp75 DNA molecules with 1 unit of T4 DNA ligase in 20 μl reaction for 3 h at room temperature. The ligation mixture was used to transform E. coli strain DH5α. Ampicillin-resistant bacterial colonies were analyzed by agarose gel slot lysis method for the presence of plasmid DNA of appropriate size. Plasmid DNA from 15 transformants was isolated, analyzed by restriction enzyme digestion, and partially sequenced to determine the number of bases deleted from the carboxyl terminus and to confirm the addition of termination linker.

A transient transfection method was developed and optimized to study the intracellular distribution of gp75 expressed by mutant constructs. Briefly, 2–4×10⁴ SK-MEL-23 clone 22a melanoma cells and mouse L cells fibroblasts were plated in 8-well LabTek chamber slides. The cells were transfected with plasmid DNA by calcium phosphate precipitate method for 16–24 h, and then allowed to accumulate the expressed protein for 12 to 48 h which was evaluated by immunofluorescence microscopy and immunoelectronmicroscopy.

For immunofluorescence microscopy, cells on the 8-well glass slides were fixed with formaldehyde, followed by methanol, and stained with gp75 specific mouse mAb TA99 or OKT-8 followed by FITC-conjugated anti-mouse IgG. Cells were examined under Nikon Optiphot fluorescence microscope and photographed using Kodak Ektachrome film.

For immunoelectronmicroscopy, mAb TA99 directly conjugated to 10 nm gold particles was used for localization of gp75 by immunoelectron microscopy. Colloidal gold was prepared as described (Smit and Todd, 1986) and mAb TA99-gold conjugate was prepared according to Alexander et al., 1985. Human melanoma SK-MEL-19 cells were fixed with 0.2% glutaraldehyde in 0.1 M phosphate buffer, pH 7.4, infused with 2.3 M sucrose in PBS and the cell pellet was then frozen in liquid nitrogen. Ultrathin sections were cut and collected on formvar-carbon coated nickel grids. The sections on the grids were incubated in 0.5% BSA in PBS to block nonspecific protein binding sites and then stained with mAb TA99 conjugated to 10 nm gold particles. Washing and staining of the sections was performed according to Griffiths et al., 1983. Sections were observed on a Jeol 100CX electron microscope.

These experiments showed that the expressed proteins from constructs having a sorting region that included the 36 amino acid cytoplasmic tail of human gp75 (with or without the transmembrane region) were localized to the juxtanuclear region of the cells, and there was little or no staining of other cytoplasmic structures of the plasma membrane. This pattern showed localization of the expressed protein in the Golgi region and possible other organelles such as late endosomes and lysosomes present in the Golgi region. It was further determined, however, that the absence of cell surface staining which would be expected because of the presence of the CD8 portion of the chimeric protein is probably the result of protease degradation of the CD8 within the protease-rich endosomes and lysosomes.

EXAMPLE 6

The role of specific N-glycans in determining stability of an endocytic membrane protein within different cellular compartments was investigated. The tyrosinase family of glycoproteins has multiple conserved potential N-linked glycosylation sites. The mouse brown locus protein, gp75, is a prototype of the TRP family. We examined how N-linked glycosylation on gp75 plays a role in maintaining the stability of this protein as it is transported through different compartments, by systemically eliminating each N-linked glycosylation sites.

An 1.8 Kb EcoR I fragment containing the full length mouse gp75 cDNA was isolated from pMT4 plasmid (kindly provided by Dr. T. Shibahara, Tohoku University School of Medicine, Japan), and subcloned into the unique EcoR I site of eukaryotic expression vector pSVK3.1 to generate pSVK3.1-mgp75. pSVK3.1 is a derivative of pSVK3 (Pharmacia LKB Biotechnology, Inc., Piscataway, N.J.), modified by removing the Sac I fragment within the multiple cloning sites. The orientation of the insert was determined by restriction enzyme analysis and confirmed by DNA sequencing using Sequenase Kit (US Biochemicals, Cleveland, Ohio). The Muta-gene Phagemid in vitro mutagenesis kit (Bio-Rad, Melvile, N.Y.) was used to create Asn to Gln mutations at amino acid positions 96, 104, 181, 304, 350 and 385, using the following oligonucleotides respectively.

OLXU 27: 5'-CTGACATGTTCTCTGAAAGAACCTCAGAGG-3'; SEQ ID NO. 21

OLXU 28: 5'-GTGTCCTGAGAACTGATCATTGCACTGACA-3'; SEQ ID NO. 22

OLXU 29: 5'-ATAAACGGAAATCTGCTCAAATTGTGGTGT-3'; SEQ ID NO. 23

OLXU 30: 5'-ACCCTCAGTGCTCTGACAAAGTGTTCCCAG-3'; SEQ ID NO. 24

OLXU 31: 5'-ACTGTCTGTAGACTGGGAATAAAAAGGAGG-3'; SEQ ID NO. 25

OLXU32: 5'-TCCTCCCGTTCCCTGCAGGAAGAGGTG-3'. SEQ ID NO. 26

Mutagenesis with above mutagenic primers resulted in conversions of Asn (AAC or AAT) to Gln (CAG) at respective sites. The resulting mutant constructs were designated gp75g1, gp75g2, gp75g3, gp75g4, gp75g5 and gp75g6. Mutants were screened and identified by DNA sequencing.

Mouse L cell fibroblasts were transfected with plasmids containing full-length or mutant gp75 cDNA and pSV2 neo using calcium phosphate precipitation method. The transfectants were selected for growth in medium containing 500 μg/ml effective concentration of antibiotic Geneticin (GIBCO BRL Life Technologies, Grand Island, N.Y.). Individual transfectant clones were isolated using cloning rings (Bellco, Vineland, N.J.) and screened for gp75 expression by immunofluorescence staining with mAb TA99.

We first investigated which potential N-linked glycosylation sites were used by comparing the molecular mass difference of mutant gp75 proteins to immature, glycosylated wild-type gp75. Transfectants expressing different gp75 glycosylation mutants were labeled with [$^{35}$S] methionine for 15 min followed by immunoprecipitation with mAb TA99. B16 melanoma cells and wild-type gp75 transfectants produced a sharp 71 kDa band of gp75, representing an immature form of gp75 with high mannose sugar chains characteristic of ER processing. Among the glycosylation mutants, only gp75g2 appeared as a 71 kDa band, while all others produced a 68 kDa band. Because one high mannose oligosaccharide chain corresponds to approximately 3 kDa of molecular mass, the observed difference between the molecular mass of the mutant gp75 proteins and wild-type gp75 is consistent with the interpretation that the 68 kDa mutant gp75 molecules contained one less carbohydrate chain than the wild-type gp75. This, in turn, is a direct result of the abolishment of one carbohydrate chain at the particular potential glycosylation site. Thus, it is reasoned that these sites (Asn positions 96, 181, 304, 350 and 385 which are individually mutated in gp75g1, g3, g4, g5 and g6) are normally used for glycosylation. In contrast, the mutation at Asn 104 (mutated in gp75g2) did not cause any alteration in molecular mass between gp75g2 and wild-type gp75; it is most likely that this site is normally not used for glycosylation.

To assess the individual roles of each N-glycan in the stability and transport of mouse gp75, we performed pulse-chase metabolic labeling with [$^{35}$S]methionine followed by immunoprecipitation and Endo H digestion on each mutant gp75 transfectant, and compared the data to that of wild-type mouse gp75 expressed in L cell transfectants. Newly synthesized wild-type gp75 appeared as a doublet of 70 kDa and 68 kDa bands in the transfectants at the end of 15 pulse and after a subsequent 15 min, or 30 min chase. Endo H digestion reduced the bands to 57 and 52 kDa core polypeptide bands, showing that before 30 min chase, newly synthesized gp75 remained in the ER. Starting from after 30 min chase, gp75 appeared as a mature 72–79 kDa band, which was resistant to Endo H digestion, because Endo H digestion could not remove all N-glycans to the predicted core peptide size. This indicates movement of gp75 protein from the ER or cis-Golgi (until 30 min chase) to the medial- or trans-Golgi 30 min after de novo synthesis and further processing on the carbohydrate chains in these compartment. The 72–79 kDa gp75 protein did not change further after subsequent chase, indicating completion of glycosylation on gp75. The mature gp75 is presumably further transported to the endosomes/lysosomes, although the time course is not reflected from this experiment. The intensity of the 72–79 kDa band remained stable until 4 h after chase, indicating a half-life of 4–8 h of the mature protein.

The above pulse-chase experiment followed by immunoprecipitation with mAb TA99 and Endo H digestion reflecting the intracellular stability as well as protein transport from the ER to the Golgi was performed on all of the glycosylation mutants. The cellular transport and stability of all the glycosylation mutants can be grouped into 3 categories. (1) gp75g1 and gp75g3 appeared to have very similar transport pattern and stability data as that of the wild-type gp75; (2) gp75g4 and gp75g6 proteins remained Endo H sensitive with half-lives between 1–4 h, suggesting retention and degradation in the ER; (3) gp75g5 was transported from the ER to the Golgi in a similar rate as the wild type gp75, yet displayed a shorter half life. At the end of 15 min pulse labeling and 30 min chase, gp75g5 appeared as a 68 kDa which was sensitive to Endo H to yield a 57 kDa band. (The additional 66 kDa band with a core polypeptide of 52 kDa is a truncated form similar to that in full length transfectants). At the end of 1 h chase, majority of gp75g5 was converted to an Endo H resistant 75 kDa band, showing that it was transported and processed to the medial- or trans-Golgi, and the rate of transport was similar to that in wild-type transfectants. Unlike that of the wild-type gp75, the intensity of the 75 kDa band decreased after 1 h of chase. This suggested that the half life of gp75g5 was between 1 to 4 h, shorter than wild type gp75 in transfectants (T 1/2=4–8 h). Apparently, the abolishment of the N-linked carbohydrate chain at position 350 affected the stability of the protein.

The above data showed that gp75g5 had a shorter half life than wild-type gp75. It appeared to be transported to the Golgi, and presumably further to the endosomes/lysosomes, as the transport signal in the cytoplasmic tail is intact. In order to examine whether gp75g5 was actually transported to the endosomes/lysosomes and the shorter half-life of the protein was due to endosomal/lysosomal degradation, we repeated the pulse-chase experiment in the presence of NH$_4$Cl, a lysosomotrophic weak amine which inhibits proteases in acidic environments such as endosomes or lysosomes, or leupeptin, a serine/cysteine protease inhibitor which inhibits mainly proteases in the lysosomes. At the end of 15 min label, the 68 kDa mutant gp75 band was synthesized with equal intensity in the absence or presence of NH$_4$Cl incubation. With the absence of NH$_4$Cl, the intensity of gp75g5 band reduced markedly at 4 h chase comparing with that at 0.5 h chase. However, in the presence of NH$_4$Cl, the gp75g5 band was nearly as strong at the end of 4 h chase as at the end of 0.5 h chase or after 15 min labeling. This result clearly showed a prolonged half-life to more than 4 h for gp75g5 in the presence of NH$_4$Cl, and suggested that the short half life of gp75g5 was due to rapid degradation in acidic compartments sensitive to NH$_4$Cl inhibition, which are most likely the late endosomes or lysosomes. Similarly, in the presence of leupeptin, the intensity of the gp75g5 band remained as the same after 4 h chase as after 0.5 h chase, showing a great stabilization of the protein. Based on these results, it is concluded that gp75g5 was transported to the endosomes/lysosomes, and was rapidly degraded there.

The above conclusion is also confirmed by immunofluorescence staining of transfectants expressing gp75g5 in the absence and presence of leupeptin. In wild-type gp75 transfectants, gp75 is localized in the juxtanuclear patches and peripheral punctuate vesicles, which represent the Golgi complex and the late endosomes/lysosomes. The juxtanuclear patches represented Golgi apparatus, and the localization of wild-type full-length gp75 in the Golgi apparatus at steady state suggested accumulation and slow passage of gp75 in this compartment during transport. The staining of gp75g5 transfectants showed only intensive juxtanuclear structures, with no visible peripheral vesicles. The lack of staining of peripheral vesicles indicated that at steady state, there was no detectable level of gp75g5 in the endosomes and lysosomes. However, staining of gp75g5 transfectants in the presence of leupeptin revealed an enhanced overall staining of gp75g5 transfectants, particularly, the peripheral vesicles became visible. These peripheral vesicles are most likely endosomes and lysosomes based on studies on the location of wild-type gp75 in the transfectants. This result supports the above notion that leupeptin stabilized the gp75g5 mutant proteins in endosomes and lysosomes.

Taken together, the above data showed that the mutation at Asn 350 to eliminate an oligosaccharide chain at this position produced a mutant gp75 protein, which is more prone to proteolytic digestions in the lysosomes than the wild-type gp75, and serine or cysteine proteases were involved in the degradation process. This mutation did not alter the route of intracellular sorting and trafficking of gp75, as gp75g5 was still sorted to the endosomes/lysosomes.

Pulse-chase experiments of gp75gl and gp75g3 showed very similar pattern of gp75 transport and stability compared to the wild-type gp75. This result indicated that the N-glycans at Asn 96 and 181 (eliminated at gp75gl and g3) are not involved in determine the stability of gp75. Under immunofluorescence staining, gp75gl was localized to juxtanuclear structure and peripheral vesicles, just like the localization of wild-type gp75. Staining gp75g3 revealed predominantly perinuclear vesicles with non-visible juxtanuclear patches, suggesting localization of gp75g3 mainly in the endosomes and lysosomes at steady state. Since the juxtanuclear patches are most probably the Golgi complex or early endosomes, this result suggested an increased rate of transport of gp75g5 through the Golgi complex and the early endosomes than that of wild-type gp75. Thus, N-glycan at Asn 181 seems to be involved in the rate of transport through the Golgi.

Pulse-chase experiments of gp75g4 and gp75g6 showed a different pattern of cellular transport and stability from that of wild-type gp75 or other glycosylation mutants. After 15 min pulse and after up to 4 h chase, gp75g4 and gp75g6 mutant proteins remained to be 68 kDa, sensitive to Endo H digestion; and their intensities decreased between 1 to 4 h of chase. These data suggested ER retention and degradation of the mutant proteins. Under immunofluorescence staining with mAb TA99, gp75g4 showed a pattern of weak, diffuse staining mainly in fine perinuclear networks, indicative of the ER network; while gp75g6 was mainly localized in condensed perinuclear patches, which was consistent to be the Golgi apparatus. Combining the biochemical and staining data, it appears that gp75g4 is retained in the ER and gp75g6 is retained mostly in the cis-Golgi apparatus. Thus, the elimination of N-glycan at Asn 304 or Asn 385 affected the cellular transport of the protein from the ER to the Golgi. Malfolding may be the mechanism for the retention as suggested by a lot of earlier studies.

What is claimed is:

1. A nucleic acid construct for genetic immunization comprising
   (a) an antigen-coding region encoding an antigenic protein or peptide; and
   (b) a sorting region encoding a protein or peptide which acts as a sorting signal to direct intracellular transport of the protein or peptide to the endosomes or the endoplasmic reticulum of a cell.

2. The construct of claim 1, further comprising a linker region disposed between the antigen-coding region and the sorting region.

3. The construct according to claim 2, wherein the sorting region is derived from the human brown locus protein, gp75; human albino locus protein, tyrosinase; human silver locus protein, Pmel 17; or human pink eyed locus P-protein.

4. The construct according to claim 2, wherein the sorting region includes at least a peptide selected from among the peptides given by Seq. ID Nos. 1–5.

5. The construct of claim 4, further comprising a promoter region effective to permit expression of the construct in mammalian cells.

6. The construct according to claim 1, wherein the sorting region is derived from the human brown locus protein, gp75; human albino locus protein, tyrosinase; human silver locus protein, Pmel 17; or human pink eyed locus P-protein.

7. The construct according to claim 1, wherein the sorting region encodes at least the peptide Glu Ala Asn Gin Pro Leu Leu Thr Asp (SEQ ID NO. 1).

8. The construct according to claim 1, wherein the sorting region encodes at least the peptide Glu Glu Lys Gin Pro Leu Leu Met Asp (SEQ ID NO. 2).

9. The construct according to claim 1, wherein the sorting region encodes at least the peptide Glu Asp Ser Pro Leu Leu (SEQ ID NO. 3).

10. The construct according to claim 1, wherein the sorting region encodes at least the peptide Glu Asp Thr Pro Leu Leu (SEQ ID NO. 4).

11. The construct according to claim 10, further comprising a promoter region effective to permit expression of the construct in mammalian cells.

12. The construct according to claim 11, wherein the promoter region is selected from among the SV40 promoter, the CMV promoter and the RSV promoter.

13. The construct according to claim 1, wherein the sorting region encodes at least the peptide sequence Pro Ser Arg Asp Arg Ser Arg His Asp Lys Ile His (SEQ ID NO. 5).

14. The construct according to claim 1, wherein the sorting region is a mutant form in which a glycosylation site present in a corresponding wild type sorting region has been altered.

15. A composition to elicit an immune response against a target antigen comprising a nucleic acid construct comprising:
   (a) an antigen-coding region encoding an antigenic protein or peptide; and
   a sorting signal encoding a protein or peptide which acts as a sorting signal to direct intracellular transport of the protein or peptide into the endosomes or the endoplasmic reticulum of a cell, wherein the nucleic acid construct is effective to elicit an immune response against the target antigen when administered to a subject individual.

16. The composition according to claim 15, wherein the nucleic acid construct is packaged in a liposome.

17. The composition according to claim 15, wherein the nucleic acid construct is coated on a colloidal gold particle.

18. The composition according to claim 15, wherein the nucleic acid construct is incorporated into a viral expression vector.

19. The composition according to claim 15, wherein the sorting region is derived from the human brown locus protein, gp75; human albino locus protein, tyrosinase; human silver locus protein, Pmel 17; or human pink eyed locus P-protein.

20. The composition according to claim 15, wherein the sorting region includes at least a peptide selected from among the peptides given by Seq. ID Nos. 1–5.

21. A method for inducing an immune response to an antigen in a mammal, comprising the step of administering to the mammal a nucleic acid construct according to claim 1.

22. The method according to claim 21, wherein the sorting region is derived from the human brown locus protein, gp75; human albino locus protein, tyrosinase; human silver locus protein, Pmel 17; or human pink eyed locus P-protein.

23. The method according to claim 21, wherein the sorting region includes at least a peptide selected from among the peptides given by Seq. ID Nos. 1–5.

24. A method for preparing a composition for eliciting an immune response comprising the step preparing a nucleic acid construct according to claim 1.

25. The method according to claim 24, further comprising the step of packaging the nucleic acid construct in a liposome carrier.

26. The method according to claim 24, further comprising the step of coating the nucleic acid construct on a colloidal gold particle.

27. The method according to claim 24, wherein the nucleic acid construct is incorporated into a viral expression vector.

28. The method according to claim 24, wherein the sorting region is derived from the human brown locus protein, gp75; human albino locus protein, tyrosinase; human silver locus protein, Pmel 17; or human pink eyed locus P-protein.

29. The method according to claim 24, wherein the sorting region includes at least a peptide selected from among the peptides given by Seq. ID Nos. 1–5.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 9
      (B) TYPE: amino acid
      (D) TOPOLOGY: linear (ii) MOLECULE TYPE:
      (A) DESCRIPTION: peptide (iii) HYPOTHETICAL: no (v) FRAGMENT TYPE: internal (vi) ORIGINAL SOURCE:
      (A) ORGANISM: human (xi) SEQUENCE DESCRIPTION: SEQ ID NO:1:

Glu Ala Asn Gln Pro Leu Leu Thr Asp
              5

(2) INFORMATION FOR SEQ ID NO:2:

(i) SEQUENCE CHARACTERISTICS:
      (A) LENGTH: 9
      (B) TYPE: amino acid
      (D) TOPOLOGY: linear (ii) MOLECULE TYPE:
      (A) DESCRIPTION: peptide (iii) HYPOTHETICAL: no (v) FRAGMENT TYPE: internal (vi) ORIGINAL SOURCE:
      (A) ORGANISM: human (xi) SEQUENCE DESCRIPTION: SEQ ID NO:2:

Glu Glu Lys Gln Pro Leu Leu Met Asp
              5

(2) INFORMATION FOR SEQ ID NO:3:

(i) SEQUENCE CHARACTERISTICS:
        (A) LENGTH: 5
        (B) TYPE: amino acid
        (D) TOPOLOGY: linear (ii) MOLECULE TYPE:
        (A) DESCRIPTION: peptide (iii) HYPOTHETICAL: no (v) FRAGMENT TYPE: internal (vi) ORIGINAL SOURCE:
        (A) ORGANISM: human (xi) SEQUENCE DESCRIPTION: SEQ ID NO:3:

Asp Ser Pro Leu Leu
                 5

(2) INFORMATION FOR SEQ ID NO:4:

(i) SEQUENCE CHARACTERISTICS:
        (A) LENGTH: 6
        (B) TYPE: amino acid
        (D) TOPOLOGY: linear (ii) MOLECULE TYPE:
        (A) DESCRIPTION: peptide (iii) HYPOTHETICAL: no (v) FRAGMENT TYPE: internal (vi) ORIGINAL SOURCE:
        (A) ORGANISM: human (xi) SEQUENCE DESCRIPTION: SEQ ID NO:4:

Glu Asp Thr Pro Leu Leu
                 5

(2) INFORMATION FOR SEQ ID NO:5:

(i) SEQUENCE CHARACTERISTICS:
        (A) LENGTH: 12
        (B) TYPE: amino acid
        (D) TOPOLOGY: linear (ii) MOLECULE TYPE:
        (A) DESCRIPTION: peptide (iii) HYPOTHETICAL: no (v) FRAGMENT TYPE: internal (vi) ORIGINAL SOURCE:
        (A) ORGANISM: human (xi) SEQUENCE DESCRIPTION: SEQ ID NO:5:

Pro Ser Arg Asp Arg Ser Arg His Asp Lys Ile His
                 5                  10

(2) INFORMATION FOR SEQ ID NO:6:

(i) SEQUENCE CHARACTERISTICS:
        (A) LENGTH: 9
        (B) TYPE: amino acid
        (D) TOPOLOGY: linear (ii) MOLECULE TYPE:

(A) DESCRIPTION: peptide (iii) HYPOTHETICAL: no (v) FRAGMENT TYPE: internal (vi) ORIGINAL SOURCE:
        (A) ORGANISM: human (xi) SEQUENCE DESCRIPTION: SEQ ID NO:6:

Ser Gly Gly Ser Gly Gly Ser Gly Gly
            5

(2) INFORMATION FOR SEQ ID NO:7:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: yes (xi) SEQUENCE DESCRIPTION: SEQ ID NO:7:

CGCCACCAGA CATAATAGC                                            19

(2) INFORMATION FOR SEQ ID NO:8:

(i) SEQUENCE CHARACTERISTICS:
        (A) LENGTH: 45
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:8:

GCCTCCTGAA CCTCCGGAAC CACCAGAAGG GGAAACACAT CTGCC               45

(2) INFORMATION FOR SEQ ID NO:9:

(i) SEQUENCE CHARACTERISTICS:
        (A) LENGTH: 48
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: yes (xi) SEQUENCE DESCRIPTION: SEQ ID NO:9:

TCTGGTGGTT CCGGAGGTTC AGGAGGCATC ATTACCATTG CTGTAGTG            48

(2) INFORMATION FOR SEQ ID NO:10:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:10:

GGTTGCTTCG GTACCTGCTG CG                                                    22

(2) INFORMATION FOR SEQ ID NO:11:

(i) SEQUENCE CHARACTERISTICS:
            (A) LENGTH: 19
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: yes (xi) SEQUENCE DESCRIPTION: SEQ ID NO:11:

CGCCACCAGA CATAATAGC                                                        19

(2) INFORMATION FOR SEQ ID NO:12:

(i) SEQUENCE CHARACTERISTICS:
            (A) LENGTH: 22
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:12:

GGTTGCTTCG GTACCTGCTG CG                                                    22

(2) INFORMATION FOR SEQ ID NO:13:

(i) SEQUENCE CHARACTERISTICS:
            (A) LENGTH: 42
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: yes (xi) SEQUENCE DESCRIPTION: SEQ ID NO:13:

CTCAGCATAG CGTTGATAGT GATTCTTGGT GCTTCTAGAA CG                              42

(2) INFORMATION FOR SEQ ID NO:14:

(i) SEQUENCE CHARACTERISTICS:
            (A) LENGTH: 42
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:14:

CGTTCTAGAA GCACCAAGAA TCACTATCAA CGCTATGCTG AG         42

(2) INFORMATION FOR SEQ ID NO:15:

(i) SEQUENCE CHARACTERISTICS:
            (A) LENGTH: 21
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: yes (xi) SEQUENCE DESCRIPTION: SEQ ID NO:15:

GAGTGCAGGC TGGTTGGCTT C         21

(2) INFORMATION FOR SEQ ID NO:16:

(i) SEQUENCE CHARACTERISTICS:
            (A) LENGTH: 21
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:16:

CCTGCACTCA CTGATCACTA T         21

(2) INFORMATION FOR SEQ ID NO:17:

(i) SEQUENCE CHARACTERISTICS:
            (A) LENGTH: 31
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:17:

TACTGCTATG GCAATGATAT CAGGTACACT A         31

(2) INFORMATION FOR SEQ ID NO:18:

(i) SEQUENCE CHARACTERISTICS:
            (A) LENGTH: 30
            (B) TYPE: nucleic acid
            (C) STRANDEDNESS: single
            (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:18:

GCGTCTGGCA CGAAGCTTAT AAGAAGCAGT                                30

(2) INFORMATION FOR SEQ ID NO:19:

(i) SEQUENCE CHARACTERISTICS:
        (A) LENGTH: 31
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:19:

GTCTTCGGTT CCTAAGCTTG CAGTAAAGGG T                              31

(2) INFORMATION FOR SEQ ID NO:20:

(i) SEQUENCE CHARACTERISTICS:
        (A) LENGTH: 12
        (B) TYPE: nucleic acid
        (C) STRANDEDNESS: single
        (D) TOPOLOGY: linear (ii) MOLECULE TYPE: other DNA (iii) HYPOTHETICAL: no (iv) ANTI-SENSE: no (xi) SEQUENCE DESCRIPTION: SEQ ID NO:20:

CTAGCTAGCT AG                                                   12

(2) INFORMATION FOR SEQ ID NO:21:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:21:

CTGACATGTT CTCTGAAAGA ACCTCAGAGG                                30

(2) INFORMATION FOR SEQ ID NO:22:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:22:

GTGTCCTGAG AACTGATCAT TGCACTGACA                                    30

(2) INFORMATION FOR SEQ ID NO:23:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:23:

ATAAACGGAA ATCTGCTCAA ATTGTGGTGT                                    30

(2) INFORMATION FOR SEQ ID NO:24:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:24:

ACCCTCAGTG CTCTGACAAA GTGTTCCCAG                                    30

(2) INFORMATION FOR SEQ ID NO:25:

(i) SEQUENCE CHARACTERISTICS:
        (A) LENGTH: 30
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:25:

ACTGTCTGTA GACTGGGAAT AAAAAGGAGG                                    30

(2) INFORMATION FOR SEQ ID NO:26:

(i) SEQUENCE CHARACTERISTICS:
        (A) LENGTH: 27
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (xi) SEQUENCE DESCRIPTION: SEQ ID NO:26:

TCCTCCCGTT CCCTGCAGGA AGAGGTG                                       27